(12) United States Patent
Sutherland

(10) Patent No.: US 6,789,022 B2
(45) Date of Patent: Sep. 7, 2004

(54) METHOD FOR ASSAYING CLUSTERED DNA DAMAGES

(75) Inventor: Betsy M. Sutherland, Wading River, NY (US)

(73) Assignee: Brookhaven Science Associates LLC, Upton, NY (US)

( * ) Notice: Subject to any disclaimer, the term of this patent is extended or adjusted under 35 U.S.C. 154(b) by 328 days.

(21) Appl. No.: 09/837,560

(22) Filed: Apr. 18, 2001

(65) Prior Publication Data

US 2002/0031770 A1 Mar. 14, 2002

Related U.S. Application Data

(60) Provisional application No. 60/198,681, filed on Apr. 20, 2000.

(51) Int. Cl.[7] .......................... G01N 33/00; G01N 33/48; G01N 33/559; C12Q 1/68
(52) U.S. Cl. .......................... 702/23; 702/19; 702/127; 435/6; 435/18; 435/183; 204/456
(58) Field of Search ............................ 702/19, 23, 127, 702/27; 435/6, 18, 183, 173.1; 204/456, 157.44, 157.63

(56) References Cited

PUBLICATIONS

Sutherland et al. (PNAS (2000) vol. 97, No. 1, pp. 103–108).*
J.F. Ward, *Radiation Res. 104*: S103–S111 (1985).
J.F. Ward, *Int. J. Radiation Biol. 66*: 427–432 (1994).
S.S. Wallace, *Radiation Res. 150* (Sup. 5): S60–S79 (1998).
P.L. Olive, *Radiation Res. 150*: S42–S51 (1998).
Chaudhry and Weinfeld, *J. Biol. Chem. 272*: 15650–15655 (1997).
Harrison et al., *Nucleic Acids Res. 26*: 932–941 (1998).
Makrigiorgos et al., *Int. J. Radiation Biol. 74*: 99–109 (1998).
Sutherland et al., *Anal. Biochem. 239*: 53–60 (1996).
Sutherland et al., *Anal. Biochem. 163*: 446–457 (1987).
Freeman et al., *Anal. Biochem. 158*: 119–129 (1986).
Milligan et al., *Radiation Res. 151*: 334–342 (1999).
Prise et al., *Carcinogenesis 20*: 905–909 (1999).
Chen and Sutherland, *Electrophoresis 10*: 318–326 (1989).

* cited by examiner

*Primary Examiner*—Marjorie Moran
*Assistant Examiner*—Lori A. Clow
(74) *Attorney, Agent, or Firm*—Margaret C. Bogosian

(57) ABSTRACT

Disclosed is a method for detecting and quantifying clustered damages in DNA. In this method, a first aliquot of the DNA to be tested for clustered damages with one or more lesion-specific cleaving reagents under conditions appropriate for cleavage of the DNA to produce single-strand nicks in the DNA at sites of damage lesions. The number average molecular length ($L_n$) of double stranded DNA is then quantitatively determined for the treated DNA. The number average molecular length ($L_n$) of double stranded DNA is also quantitatively determined for a second, untreated aliquot of the DNA. The frequency of clustered damages ($\Phi_c$) in the DNA is then calculated.

27 Claims, 5 Drawing Sheets

| Enzyme | Principal Lesion Class Recognized | Lesions Recognized |
|---|---|---|
| E. coli formamidopyrimidine-DNA glycosylase (Fpg Protein) | Oxidized Purines | FaPyAdenine, FaPyGuanine, C8-oxoGuanine, some abasic sites, C8-oxoAdenine and to a lesser extent, other modified purines (FaPy = 2,6-diamino-4-hydroxy-5-N-methylformamido-pyrimidine). |
| E. coli Nth Protein (Endonuclease III) | Oxidized pyrimidines | Thymine residues damaged by ring saturation, fragmentation, or ring contraction, including 5,6-dihydrothymine, thymine glycol, urea, 5-hydroxy-5-methyl hydantoin, DNA damaged at guanine sites, and some abasic sites. |
| E. coli Nfo Protein (Endonuclease IV) | Abasic sites | Several types of abasic sites, including oxidized abasic sites, abasic sites modified with alkoxyamines, and DNA containing urea residues. |

FIG. 1

METHOD FOR ASSAYING CLUSTERED DNA DAMAGES

This application claims benefit of U.S. Provisional Application No. 60/198,681 filed Apr. 12, 2000.

The present invention was made with Government support under contract number DE-AC02-98CH10886, awarded by the U.S. Department of Energy. The Government has certain rights in the invention.

BACKGROUND OF THE INVENTION

Ionizing radiation may produce cancer, death and loss of neural function in humans and animals, and induce killing, mutation and chromosomal aberrations in cells [Bissell et al., (1997) *Modeling Human Risk: Cell and Molecular Biology in Context,* Lawrence Berkeley National Laboratory, Univ. of California, Berkeley]. Humans are exposed to low doses of radiation during air travel, from radon in homes, during space travel or in areas of low-level contamination, including former nuclear weapon production sites. Nuclear energy production facility workers may encounter higher doses of ionizing radiation than others. In addition, humans encounter higher radiation doses during radiotherapy and humans, animals and plants encounter much higher radiation doses in contaminated areas such as Chernobyl and near the sites of other nuclear mishaps [Bissell, 1997; Yang et al., *Radiation Res.* 148 (Sup. 5): S17 (1997); Tucker et al., *Radiation Res.* 148: 216 (1997); Bigbee et al., *Radiation Res.* 147: 215 (1997); Fry et al., Radiation Res. 150: 695 (1998)].

Ionizing radiation induces many different types of DNA damages [Wallace, *Radiation Res.* 150 (Sup. 5): S60 (1998)] and the identity of the specific lesion types that are responsible for the biological effects of radiation remains uncertain. Understanding the long term effects of low and high doses of ionizing radiation on living organisms requires identification of critical radiation-induced DNA lesions, assessment of their reparability and determination of the consequences of misrepaired or unrepaired, persistent lesions.

Lethal and mutagenic effects of ionizing radiation result principally from incompletely or incorrectly repaired DNA lesions [Ward, *Radiation Res.* 104: S103 (1985) and *Int. J. Radiation Biol.* 66: 427 (1994)]. Ionizing radiation induces high levels of isolated DNA lesions, including single strand breaks (SSBs), damaged bases and abasic sites that are located at a distance from other damages (Wallace, 1998). Such isolated damages are generally repaired efficiently, and their repair may be enhanced by priming ionizing radiation doses [Le et al., *Science* 280: 1066 (1998)]. Ionizing radiation also induces closely spaced lesions, including double strand breaks (DSBs) that result from two or more single strand breaks being induced on opposing DNA strands within 10–20 base pairs of one another [Van Der Schans, *Int. J. Radiation Biol.* 33: 105 (1978); Olive, *Radiation Res.* 150: S42 (1998)].

It has been postulated that ionizing radiation also produces other clustered DNA damages that are composed of other closely spaced lesions on opposing DNA strands [Ward, *Radiation Res.* 86: 185 (1981)]. Although it has been postulated that such clustered DNA damages contribute significantly to the biological effects induced by radiation [Ward, 1985 and 1994; Goodhead, *Int. J. Radiation Biol.* 65: 7 (1994); Ward, *Radiation Res.* 86: 185 (1995)], it has not been possible to demonstrate their induction in genomic DNA following low doses of ionizing radiation. Therefore, it has not been possible to evaluate the biological impact of low doses of radiation by measuring DNA damage induction and repair.

Using model systems of oligonucleotides bearing defined lesions at specific relative spacings on opposing strands, it has been possible to examine model damage clusters [Chaudhry and Weinfeld, *J. Biol. Chem.* 272: 15650 (1997) and *J. Mol. Biol.* 249: 914 (1995); Harrison et al., *Nucleic Acids Res.* 26: 932 (1998)]. Such studies indicate that damage clusters may be non-repairable, highly repair-resistant, or pre-mutagenic damages. Because it has not been possible to measure damage clusters induced in genomic DNA by irradiation, it is not known whether low doses of ionizing radiation produce significant levels of clustered DNA damages in cells. In addition, the composition and frequency of damage clusters is unknown.

Ultraviolet (UV) radiation, which induces the formation of cyclobutane pyrimidine dimers in DNA, has been demonstrated to produce closely spaced cyclobutane pyrimidine dimers. UV-induced closely spaced dimers located on opposing strands of DNA have been demonstrated using an enzyme-based assay that converts the closely spaced cyclobutane pyrimidine dimers into closely spaced single strand nicks that are revealed as double strand breaks by centrifugation or electrophoretic separation techniques [Lam and Reynolds, *Radiation Res.* 166: 187 (1986)]. Because ionizing radiation induces a heterogeneous variety of damages, it has been refractory to the use of such simple assay techniques to demonstrate the induction of clustered DNA damages by ionizing radiation, particularly by low doses of ionizing radiation.

Irradiation of plasmid DNA with 900–10,000 Gy of neutrons produced short DNA fragments consistent with clustered DSBs [Pang et al., *Radiation Res.* 150: 612 (1998)]. Thermal denaturation and S1 nuclease analysis of γ-irradiated λ DNA suggested production of bulky lesions [Martin-Bertram et al., *Radiation Environ. Biophys.* 27: 305 (1983)]. S1 nuclease and gamma endonuclease treatment of λ DNA irradiated with 2,000–8,000 Gy of rays suggested the close proximity of unpaired DNA regions and base damages [Kohfeldt et al., *Radiation Environ. Biophys.* 27: 123 (1988)], and S1 analysis of human cells exposed to 100 Gy of γ-rays indicated closely spaced damages, probably nicks and gaps [Legault et al., *Mol. Cell. Biol.* 17: 5437 (1997)]. At these high radiation doses, clustered DNA damages could include sites resulting from multiple independent radiation hits and therefore these model studies do not necessarily reveal damages that are induced with low doses of radiation (physiological doses that result in high cell survival).

Makrigiorgos et al. [*Int. J. Radiation Biol.* 74: 99 (1998)] state that gel electrophoresis-based methods to detect clustered damages in DNA, such as are used in model DNA studies, cannot be applied to genomic DNAs or mixtures of DNAs of unknown DNA sizes. Therefore, as a model for the detection of ionizing radiation-induced clustered DNA damages, Makrigiorgos, et al. developed a fluorescence energy transfer method for detecting and quantifying closely spaced aldehyde-containing abasic sites that were artificially introduced into DNA by acid depurination. Based on the experiments reported below, the limit of sensitivity of the fluorescence energy transfer method has been calculated to be approximately 1 per 17,000 base pairs, which would correspond to high radiation doses (approximately 400 Gy, cf. FIG. 4). Although the fluorescence energy transfer method could be applied to the detection and quantitation of closely spaced aldehyde-containing abasic sites that may be induced by high doses of ionizing radiation, the method suffers from lack of sensitivity and the inability to detect other forms of clustered DNA damages.

The development of a sensitive method for the detection and quantitation of a variety of types of clustered DNA damages would facilitate the evaluation of the biological impact of radiation exposure. Such an assay system would be additionally useful for monitoring damage resulting from exposure to physiological doses of ionizing radiation in the home and/or workplace and in monitoring the efficacy of radiation therapy protocols. In addition, such an assay system would provide a method for assessing radiation damage to humans, crops, livestock and wildlife following a nuclear mishap.

An assay for clustered DNA damages would be additionally useful for the detection and quantification of clustered damages in DNA from biological specimens following exposure of the specimens to chemical agents, including known and suspected DNA damaging agents and known or prospective chemotherapeutic agents.

SUMMARY OF THE INVENTION

In one aspect, the present invention relates to a method for detecting and quantifying clustered damages in DNA. The method comprises contacting a first aliquot of the DNA to be tested for clustered damages with one or more lesion-specific cleaving reagents under conditions appropriate for cleavage of the DNA to produce single-strand nicks in the DNA at sites of damage lesions. The number average molecular length (Ln) of double stranded DNA is then quantitatively determined for the treated DNA. The number average molecular length (Ln) of double stranded DNA is also quantitatively determined for a second, untreated aliquot of the DNA. The frequency of clustered damages ($\Phi_c$) in the DNA is then calculated using the equation: $\Phi_c = 1/L_n$ (+enzyme)$-1/L_n$(−enzyme) wherein $L_n$(+enzyme) is the number average molecular length of double stranded DNA determined for the lesion-specific cleaving reagent-treated DNA, and $L_n$(−enzyme) is the number average molecular length of double stranded DNA determined for the untreated DNA. In a preferred embodiment, the number average molecular length of double stranded DNA is determined by size fractionation of the DNA in an aliquot using non-denaturing gel electrophoresis and quantitative electronic imaging of the fractionated DNA produced. One or more lesion-specific enzymes can be used in the method. Suitable enzymes include *E. coli* Nfo protein, *E. coli* formamidopyrimidine-DNA glycosylase, *E. coli* Nth protein. Useful combinations of enzymes are Fpg protein and endonuclease III; Fpg protein and endonuclease IV; endonuclease III and endonuclease IV; and endonuclease III, endonuclease IV and Fpg protein.

In another aspect, the present invention relates to a method for detecting and quantifying clustered damages in DNA of a biological organism induced by exposure of the biological organism to a DNA-damaging agent. This is achieved by assaying a sample for clustered damages by the above method before and after exposure to a DNA-damaging agent, with the difference of the two values being a value representative of the clustered DNA damage induced by exposure of the biological organism to the DNA-damaging agent. This method can be used to detect and quantitate DNA damaging induced by DNA-damaging agents such as X-rays, γ-rays, radon, and other known or suspected carcinogens. This method can also be used to detect and quantitate an accumulation of clustered damages in DNA of a biological organism over a period of time.

BRIEF DESCRIPTION OF THE DRAWINGS

FIG. 1 is a summary of the activities and specificities of several lesion-specific endonuclease enzymes.

DETAILED DESCRIPTION OF THE INVENTION

Figure 2:
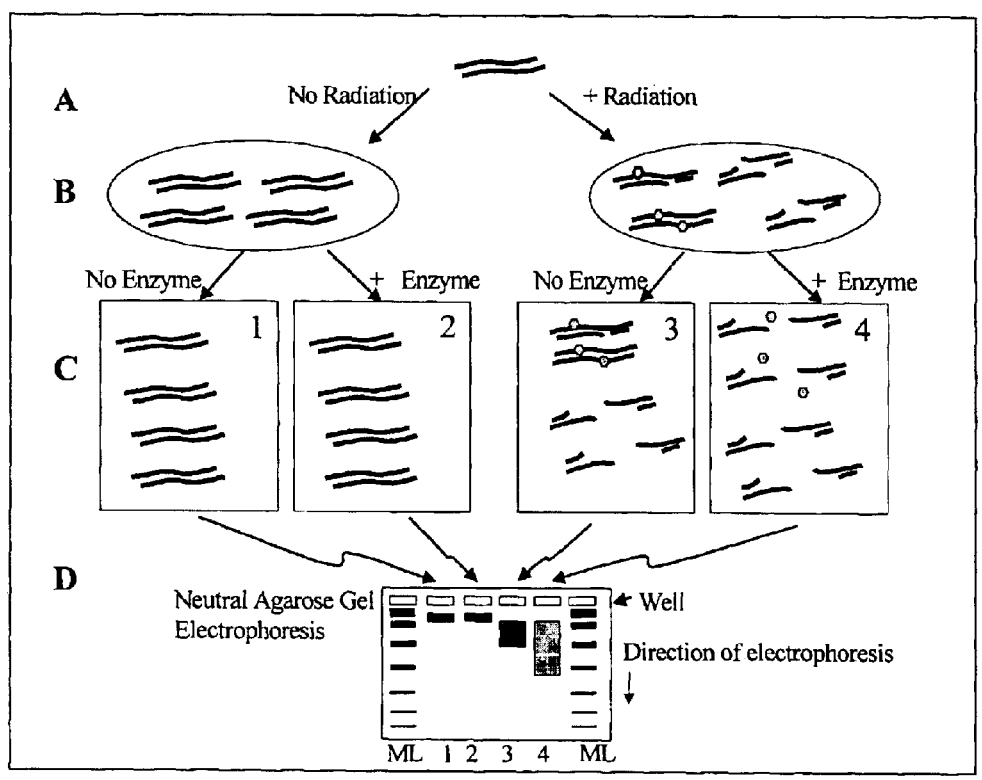
FIG. 2 is a diagrammatic representation of the principles of the clustered DNA damage assay of the subject invention utilizing ionizing radiation as the DNA damaging agent. A) DNA remains unirradiated (left) or is exposed to ionizing radiation (right). B) Unirradiated DNA is unchanged in size (left oval), whereas radiation produces DSBs and clustered lesions containing damaged bases or abasic sites at approximately equal frequencies (right oval). C) Treatment of unirradiated DNA with a lesion-specific enzyme has little or no effect on the size of the DNA molecules (block 2 relative to block 1). Irradiated DNA contains both DSBs (which reduce the size of the DNA) and clustered lesions (which do not reduce DNA size) (block 3); however, lesion-specific enzyme treatment of irradiated DNA (through release of damaged bases and AP endonuclease action) generates de novo DSBs at cluster sites (block 4). D) DNA molecules from experimental samples, along with molecular length standard DNAs (ML) are dispersed according to double strand molecular length by agarose gel electrophoresis under neutral conditions. Ionizing radiation also produces isolated DNA damages (not shown) that lesion-specific enzyme treatment converts to SSBs but not to DSBs.

The present invention is based on the development of an assay to detect clustered damages in DNA. The assay method is applicable to the determination of the effects of radiation and other DNA damaging agents on all types of double-stranded DNA and is not dependent upon prior knowledge of the size characteristics of the DNA to be assayed. Prior to the present disclosure, it was widely believed in the art that size separation-based techniques such as centrifugation or electrophoresis were not applicable to the detection and quantitation of clustered DNA damages induced in cells by ionizing radiation or by other DNA damaging agents aside from ultraviolet irradiation. However, the present invention utilizes these techniques to provide qualitative and also quantitative data of clustered damages.

The term clustered as used herein refers to relative positional spacing of two or more elements of a double-stranded DNA, wherein the elements are located within 20 bases of one another on opposing strands). Clustered damages in DNA as used herein describes lesions and/or nicks in the DNA which occur on opposing strands of the DNA within 20 bases from one another. Such damage generally results from exposure of the DNA to a DNA damaging agent. Prior to the present invention, it has not been possible to accurately detect clustered lesions on DNA. Clustered single-stranded nicks however, can be readily detected as double-stranded breaks in the DNA when size fractionated on a non-denaturing DNA gel. In the present invention, lesions in DNA are converted to single-stranded nicks. Clustered single-stranded nicks are then detected. The frequency of clustered lesions is then calculated by comparison of the amount of clustered single-stranded nicks prior to lesion conversion to the amount of single-stranded nicks after lesion conversion.

One aspect of the present invention relates to a method for detecting and quantifying clustered damages in DNA. A sample containing DNA which is to be assayed for clustered damages is first provided. A first aliquot of the DNA in the sample is contacted with one or more lesion-specific cleaving reagents under conditions appropriate for cleavage of the DNA thereby producing single-strand nicks in the DNA at sites of damage lesions. A second aliquot of the DNA is reserved as a control sample, and is preferably treated identically to the first aliquot, without the addition of lesion-specific cleaving reagents. The number average molecular length ($L_n$) of double-stranded DNA in each aliquot is then quantitatively determined. The obtained values are then used in the following equation to calculate the frequency of clustered damages ($\phi_c$) in the DNA:

$$\phi_c = 1/L_n(+\text{enzyme}) - 1/L_n(-\text{enzyme})$$

wherein $L_n(+\text{enzyme})$ is the value obtained for the number average molecular length of double-stranded DNA determined for the lesion-specific cleaving reagent-treated first aliquot DNA, and $L_n(-\text{enzyme})$ is the value obtained for the number average molecular length of double-stranded DNA determined for the untreated second aliquot DNA.

A lesion-specific cleaving reagent is comprised of one or more components which catalyze or otherwise cause cleavage of the DNA strand at or near the site of a lesion. It is important that the cleavage process does not result in strand separation in and of itself. There are at least two categories of lesion-specific cleaving reagents known in the art: chemical reagents and also lesion-specific enzymes. Individual cleaving reagent often act independently to cleave the DNA at a specific type of lesion. In addition, multiple cleaving reagents may work in concert to produce the desired cleavage (e.g., a DNA glycosylase which cleaves he N-glycosyl bond of damaged nucleotides in a DNA molecule, and a DNA endonuclease which cleaves the phosphodiester bond of the DNA molecule at abasic sites produced by the DNA glycosylase). The components of the lesion-specific cleaving reagent of the present invention can be varied to promote detection of different combinations of lesions in a given cluster. Such variation is within the ability of one of skill in the art. Chemical reagents and also lesion-specific enzymes capable of cleaving the phosphodiester bond of the DNA molecule at abasic sites are known and used in the art (e.g., E. coli Nfo protein (Endonuclease IV)). Lesion-specific enzymes capable of recognizing and cleaving the DNA at sites of oxidized purines (e.g., E. coli formamidopyrimidine-DNA glycosylase (Fpg protein)), and enzymes which recognize and cleave the DNA at sites of oxidized pyrimidines (e.g., E. coli Nth protein (Endonuclease III)) are also known.

Lesions which can be detected when present in clusters include, without limitation, abasic lesions, oxidized purines, and oxidized pyrimidines. Which lesions are detected depends upon the specificity of the lesion-specific cleaving reagent used in the method.

The number average molecular length of the double-stranded DNA is a measurement of the size distribution of a population of DNA molecules. This measurement is standard in the art, and represents the average length of the DNA molecule in a given DNA population, and is presented in units of DNA length. An increase in the number average molecular length of a DNA population upon exposure of the DNA to lesion-specific cleavage reagents indicates an increase in the frequency of double-stranded breaks in the DNA.

The number average molecular length of double-stranded DNA is generally determined by size fractionation of the DNA using non-denaturing gel electrophoresis, followed by quantitative electronic imaging of the fractionated DNA (Sutherland et al., in *Methods in Molecular Biol.: DNA Repair Protocols*, ed. Henderson, D., Humana Press, Totowa, N.J., pp. 183–202 (1999); Sutherland et al., *Anal. Biochem.* 239: 53 (1996); Sutherland et al., *Anal. Biochem.* 163: 446 (1987); Freeman et al., *Anal Biochem.* 158: 119 (1986)). Other methods of determining the number average molecular length of double-stranded DNA are equally applicable to the present invention.

In the present invention, closely opposed single strand nicks (either enzyme-generated from damage lesions, or pre-existing) are revealed as double strand breaks in the treated DNA through the non-denaturing gel electrophoresis. Quantitative results are obtained by staining gels with ethidium bromide and capturing a quantitative electronic image using a charge-coupled device-based system (Sutherland et al., 1987). Following the generation of a DNA dispersion curve, the number average molecular weight of the DNA are calculated. By comparing the calculated number average molecular weight of the DNAs with and without lesion-specific enzyme treatment the frequency of clustered damages is calculated.

In the absence of numerical quantification of the frequency of clustered damages, clustered damages in DNA can be qualitatively detected by visually comparing the fractionated products of DNA treated with the lesion-specific cleaving reagents to the fractionated products of the non-treated control DNA. The presence of a detectable increase in DNA migrating at a smaller size in the treated DNA compared to the non-treated control DNA indicates the presence of clustered damages which include DNA lesions.

The detection assay of the present invention can also be applied to detecting and quantifying clustered damages in DNA of a biological organism induced by exposure of the biological organism to a DNA-damaging agent. As detailed in the Exemplification section below, this assay has been used to show that clustered DNA damages are induced in human cells exposed to 0.1–1 Gy doses of high linear energy transfer (LET) radiation, 1 GeV $Fe^{+26}$ particles, doses that result in high cell survival. To detect the damages, a DNA sample is obtained from the biological organism in the unexposed state (e.g., prior to exposure of the organism to a DNA-damaging agent) and a second sample of DNA is obtained from the exposed organism. Each sample is assayed for the presence of clustered damages in the DNA by the above described method, either qualitatively or quantitatively. If quantitatively determined, the frequency of clustered damages determined for the unexposed DNA is subtracted from the frequency of clustered damages determined for the exposed sample, to produce a value representative of the clustered DNA damage which was induced by exposure of the organism to the DNA-damaging agent. Alternatively, an increase in the clustered damages in the DNA of the organism can be qualitatively determined by visual inspection of fractionated products from each sample, with a visually detectable increase in smaller migrating double-stranded fragments being indicative of an overall increase clustered nicks, and a corresponding overall increase in clustered damages in the exposed DNA.

The unexposed sample should be otherwise identical to the exposed samples. This unexposed sample may be obtained from the same source prior to exposure, or alternatively, may be obtained at the same time as the exposed sample, from an identical source (e.g. a portion of a clonal population) which is not exposed.

The term DNA-damaging agent as used herein refers to one or a combination of agents known to produce DNA damage. Such agents may take a number of forms, for example, a form of energy (e.g., ionizing radiation) or a chemical compound. Exposure of the organism to the DNA damaging agent will depend upon the form of the agent, and can be determined by one of skill in the art. Such agents may act directly or indirectly to produce damage. One example of an indirect activity is an agent which is metabolized into a product which then acts directly on the DNA. Other such examples of agents which act indirectly to produce damage are known by those of skill in the art. DNA-damaging agents appropriate for use in the present invention include, without limitation, X-rays, γ-rays, radon, and other known or suspected carcinogens. Also many chemotherapeutic agents function by either directly or indirectly damaging DNA.

This assay is appropriate for use on a homogenous DNA population (e.g., many copies of one isolated sequence) and alternatively on a heterogeneous DNA population (e.g., many copies of different isolated sequences, such as genomic DNA). The DNA may be isolated from a biological organism, or alternatively may be mechanically synthesized. A biological organism from which the DNA is isolated may be a population of naturally single celled organisms (prokaryotic or eukaryotic), or a population of single cells originally isolated from a multicellular organism (e.g., cells grown in cell culture or tissue culture, or cells from a tissue). It is often preferable to use a clonal population of cells in such assays. In addition, The biological organism may be a multicellular organism. In such instances, often a sample of the DNA will be obtained from a specimen or tissue taken from the organism.

The assay can also be applied to detecting and quantifying clustered damages in isolated DNA (outside of a biological organism) induced by exposure of the DNA to a DNA-damaging agent. As detailed in the Exemplification section below, this assay has been used to show that γ-irradiation of DNA in solution induces a significant level of clustered DNA damages. Results from this type of analysis can be compared to similar analysis on damages to DNA which are acquired in the context of a biological organism to provide useful information regarding processes which occur within the organism (e.g., DNA repair).

The present invention can also be used to identify a suspected DNA-damaging agent, by determining if exposure of isolated DNA or DNA within an organism induces the production of clustered DNA damages.

The accumulation of clustered damages over a period of time in DNA of a biological organism can also be monitored using the present invention. Samples of DNA are obtained form the organism at designated intervals over a designated period of time. The plurality of DNA samples is then assayed for the presence of clustered damages by one of the above-specified methods. For instance, if quantitative detection is desired, the frequency of clustered damages in each sample is determined and the values compared to one another to detect the accumulation of clustered damages in the biological organism over the period of time for which the samples were obtained. In one embodiment, the biological organism is exposed to a DNA-damaging agent over the period of time.

In another respect, this same type of method can be used to detect repair of clustered damages in DNA in an organism over time after exposure of the organism to a DNA-damaging agent. The frequency of clustered damage of the DNA in an organism is determined for a DNA sample obtained from the organism immediately following exposure of the organism, and then is subsequently re-determined for DNA samples obtained from the organism after one or more specified time intervals of recovery. A reproducibly detected decrease in the frequency of clustered damage over the course of the recovery period would indicate repair.

The assays described above also find use in detecting development of cellular resistant to a chemotherapeutic compound. Cells which grow resistant to a chemotherapeutic compound will not develop clustered lesions from exposure to the agent at the rate exhibited prior to development of resistance. Such cells often exhibit increased DNA repair.

EXEMPLIFICATION

FIG. 2 shows the principles of identification of clustered DNA damages. In A, DNA is either unirradiated or exposed to ionizing radiation. Panel B (left oval) shows that unirradiated DNA remains the same size, while (right oval) radiation induces double strand breaks and clustered damages (closely-opposed damages on opposing strands, either an oxidized base opposite a single strand break or two closely-opposed oxidized bases). Panel C (Block 1 vs. Block 2) shows that treatment with a lesion-specific enzyme does not affect the size of the unirradiated DNA. Block 3 of Panel C shows that in the absence of lesion-specific enzyme treatment, the size of the unirradiated DNA is decreased only by double strand breaks but not by clustered damages. Block 4 of Panel C shows that treatment with the lesion-specific enzyme induces a de novo double strand break at the site of each clustered damage. Panel D shows a schematic representation of a neutral pH agarose gel: comparison of lanes 1 and 2 (containing DNA from Blocks 1 and 2 of Panel C) shows that the lesion-specific enzyme does not affect the size distribution of the unirradiated DNA. Lane 3 (DNA from Block 3, Panel C) shows that radiation-induced double strand breaks reduce the size of the DNA, and lane 4 (DNA from Block 4, Panel C) shows that action of the lesion-specific enzyme results in a de novo double strand break at the site of each clustered damage, further reducing the size of the DNA.

Figure 3:
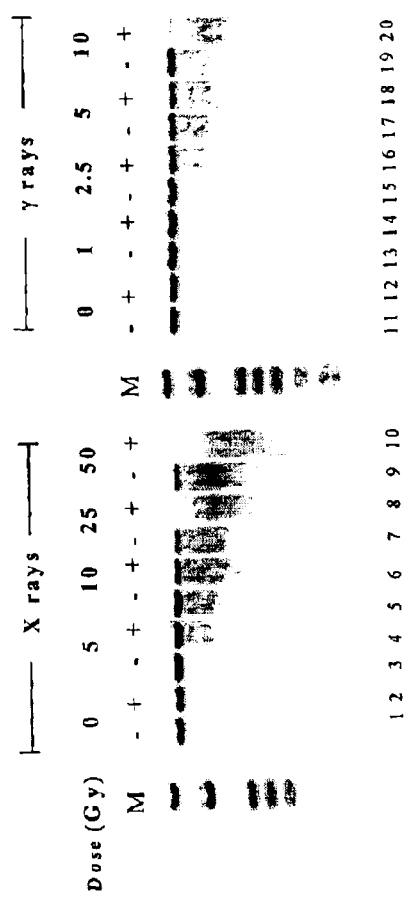
FIG. 3 is an electronic image of a neutral unidirectional pulsed field agarose gel for damage cluster analysis showing the assay of clustered oxidized purines following exposure of T7 DNA to X-rays or exposure to γ-rays and treatment or mock treatment with Fpg protein. Lanes 1–10 contain T7 DNA exposed to 0–50 Gy of 50-kVP X-rays, and lanes 11–20, T7 DNA exposed to 0–10 Gy of $^{137}$Cs γ-rays. The samples are paired, with the first of each pair not treated with enzyme, and the second, treated with Fpg protein. M lanes contain molecular length standards (λ DNA and a HindIII digest of λ DNA); unirradiated T7 DNA was also used as a length standard in calculating the DNA dispersion function.

FIG. 3 shows an electronic image of a representative neutral agarose gel for damage cluster analysis. Lanes 1–10 contain T7 DNA exposed to 0–50 Gy of 50 kVp X-rays; and lanes 11–20, T7 DNA exposed to 0–10 Gy $^{137}$Cs γ-rays. The samples are paired at each dose, with the first of each pair not treated with enzyme, and the second, treated with Fpg protein. Inspection of lanes 1, 3, 5, 7, and 9 clearly show that X-ray irradiation alone induces double strand breaks; likewise, lanes 11, 13, 15, 17, and 19 show induction of double strand breaks by γ-rays. Treatment of the unirradiated DNA with Fpg protein (lanes 2 and 12) indicates the presence of very few, if any, clustered sites in unirradiated isolated T7 DNA. However, inspection of DNAs treated with Fpg protein after irradiation (for X-rays, lanes 4, 6, 8, and 10; and for γ-rays, lanes 14, 16, 18, and 20) clearly shows that this enzyme induces de novo double strand breaks, over those induced by the radiation alone. These de novo double strand breaks represent sites of clustered damage revealed by Fpg protein treatment.

Figure 4:
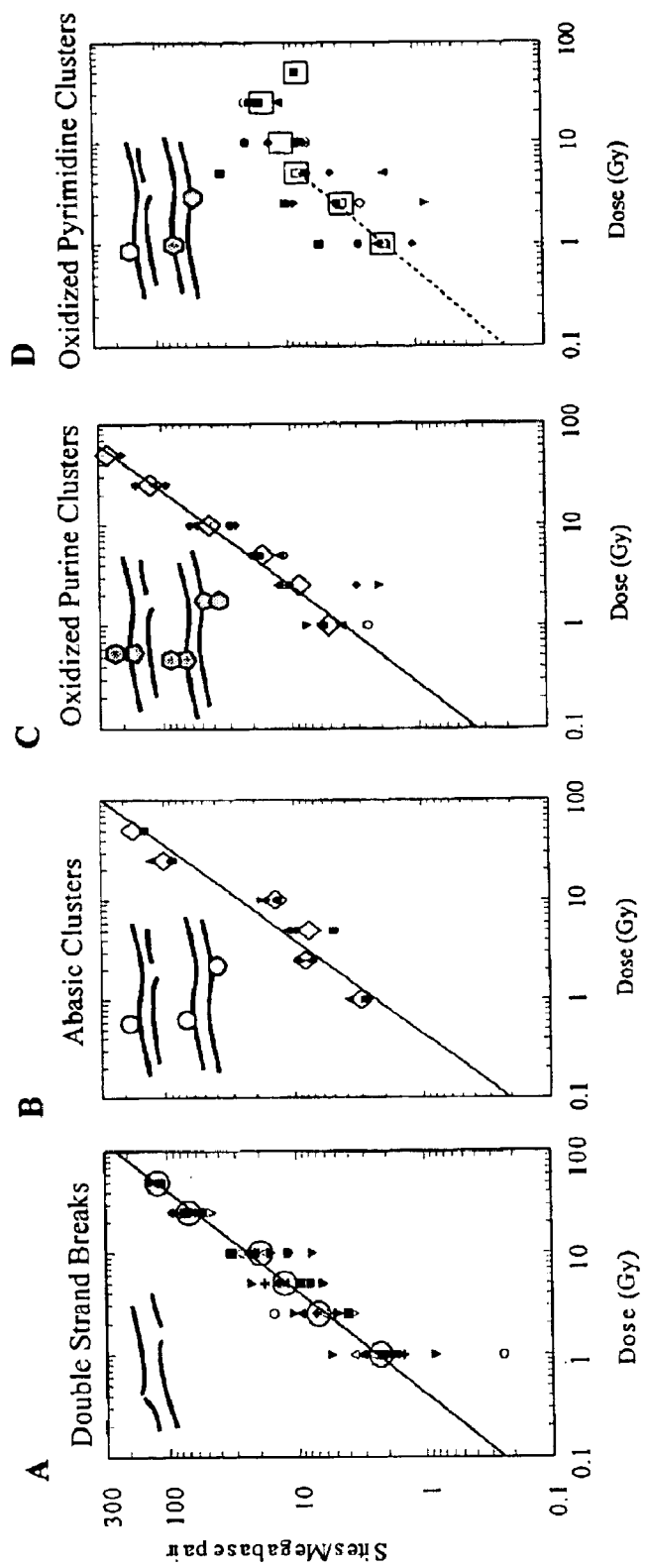
FIG. 4 is a schematic representation of the configuration of clustered lesion classes in DNA, and a graphical representation of the dose responses for clustered lesion induction in isolated T7 DNA by exposure to γ-rays. A) DSBs. B) Abasic clusters (abasic site opposite SSB, upper diagram, or abasic site, lower diagram) converted to a DSB by Nfo protein digestion. C) Oxidized purine clusters (oxidized purine opposite SSB, upper diagram, or oxidized purine, lower diagram) converted to a DSB by treatment with Fpg protein. D) Oxidized pyrimidine clusters (oxidized pyrimidine opposite SSB, upper diagram, or oxidized pyrimidine, lower diagram) converted to a DSB by treatment with Nth protein. In B–D, levels of radiation-induced DSB are subtracted. Clusters of oxidized purine opposite oxidized pyrimidine, and of multiple lesions on opposing strands are not considered. Symbols: small, results of 2–10 individual gels; large, averages; A–C, least-squares lines fit on a log-log plot of the averages of the site frequencies as a function of the doses; D, least-squares line for 0- to 5-Gy data.

FIG. 4 shows quantitative data resulting from clustered DNA damages analysis. Irradiation of isolated DNA with $^{137}$Cs γ-rays produces at least four classes of clustered damages. Panel A of FIG. 4 depicts a frank double strand break, defined functionally as two or more single strand breaks on opposite strands located within approximately 10–20 base pairs (Van Der Schans, 1978; Olive, 1998), and the yields of DSB induced by irradiation of T7 DNA in solution under our conditions. Upon electrophoresis in non-denaturing conditions, DSBs decrease the average length of a population of DNA molecules; such changes in average molecular length can be quantitated by number average length analysis (Freeman, 1986). Data are presented on a log-log plot to display both the full range of cluster yields and doses for analysis of mechanism(s) of cluster production.

In the absence of further treatment and under non-denaturing conditions, none of the other clustered lesions (FIGS. 4B–D) results in a decrease of the length of double-stranded DNA molecules. Although the frequencies of individual lesions composing the clusters may be measured by treating DNA with a lesion-specific endonuclease, followed by electrophoresis under denaturing conditions, such procedures yield the total lesion frequency, regardless of configuration as an isolated or clustered damage [see, e.g., Setlow and Carrier, *Nat. New Biol.* 241: 170 (1973); Paterson and Setlow, *Proc. Natl. Acad. Sci. USA* 69: 2927 (1972); Pouget et al., *Int. J. Radiation Biol.* 75: 51 (1999)].

To determine cluster frequencies, we combined lesion-specific DNA cleavage with subsequent analysis by quantitative, non-denaturing gel electrophoresis and electronic imaging. FIG. 4B shows that abasic clusters—a damage cluster containing at least one abasic site—are produced by γ-irradiation (1–100 Gy) of isolated T7 DNA, and can be measured by treatment with *E. coli* Nfo protein, which cleaves the phosphodiester backbone principally (FIG. 1) at abasic sites. Similarly, clustered lesions containing at least one Fpg protein site (principally oxidized purines) (FIG. 3C) are converted to frank DSBs by digestion with Fpg protein, which has glycosylase activity and nicks at apurinic sites by β lyase activity. Likewise, radiation-induced clusters containing at least one Nth protein site [principally oxidized pyrimidines (FIG. 1), (FIG. 4D)] are revealed by treatment with that enzyme. Clusters containing an oxidized purine opposite an oxidized pyrimidine with no other sites cleavable by these enzymes or single strand breaks nearby were not routinely measured. Such mixed clusters can be probed by treatment of DNA with both Fpg protein and Nth protein and other mixes of clustered damages can be probed by treatment of DNA with other combinations of glycosylases.

These studies used non-radioscavenging conditions (dilute DNA in phosphate buffer) to maximize damage yields and decrease the irradiation times at our $^{137}$Cs γ source for the largest doses from hours to minutes. The range of ionizing radiation-induced lesions depends strikingly on the level of scavengers, with single strand breaks varying almost 700-fold with high to low scavenger concentrations [Milligan et al., *Radiation Res.* 151: 334 (1999)]. Measurement of single strand breaks (SSBs) in the DNA samples shown in FIG. 4 allows us to assess the level of scavengers in our DNA solutions, and to compare with the results obtained by others. Milligan et al. (1999) obtained 66 SSB/Mb/Gy in the absence of scavengers, and 0.09 SSB/Mb/Gy in highly radioprotective solution. Prise et al. [*Carcinogenesis* 20: 905 (1999)] obtained 0.34 SSB/Mb/Gy by irradiating DNA in Tris, indicating the radioprotective nature of this solution. In phosphate buffer, we obtained 57 total breaks (and calculated 32 frank breaks), in good agreement with their data, and that for irradiation in phosphate buffer of Brake who obtained 55–67 total and 30 frank breaks [(1979) Ph.D. dissertation, Univ. Tennessee, Knoxville] and Chen and Sutherland [*Anal. Biochem.* 10: 318 (1989)] who reported 36 frank breaks. Similarly, the yields of DSB depend strongly on the scavenger levels; the yields of Prise et al. (1999) of 0.015 DSB/Mbp/Gy reflecting his highly radioprotective conditions, and ours of 2.4 DSB/Mbp/Gy the result of the low level of scavengers in our solutions. Similar DSB yields (2.1 DSB/Mbp/Gy) were obtained by Chen and Sutherland (1989).

The observation that the plots in FIG. 4 of the logarithm of double strand break frequency vs. the logarithm of the radiation dose fall close to straight lines implies that the frequency of breaks is proportional to some power of the dose and hence can be described by the equation $$\phi = \alpha D^x, \qquad \text{Eq. 3}$$

where φ is the frequency of double strand breaks induced either by irradiation alone (Eq. 1) or by irradiation followed by enzymatic treatment (Eq. 2), D is the radiation dose, α is a proportionality constant, and x is an exponent indicating the degree of the power law relationship. Experimentally, x is determined from the slope of the log-log plot from the equation $$\log \phi = x(\log \alpha + \log D). \qquad \text{Eq. 4}$$

The experimental result that x is close to unity for all the results presented in FIG. 4 (double strand breaks, 1.00; abasic clusters, 1.05; Fpg sites/oxidized purine clusters, 1.05; Nth protein sites/oxidized pyrimidine clusters, initial slope 0.94) indicates a direct proportionality between cluster lesion frequency and dose, i.e., φ=αD and thus each cluster we measure results from a single radiation track. The relative frequencies of various cluster sites per unit dose, α, are characterized on the log-log plots of FIG. 4 by the vertical displacement of the straight lines (see below).

In addition to frank strand breaks and damaged bases, ionizing radiation also produces at least three kinds of abasic sites, with only about 10% of the sites being "regular" abasic sites (the same as those produced by DNA glycosylases).

The rest are oxidized abasic sites, both 4' and (less likely) 2', with a minor fraction of 1' sites [von Sonntag, *The Chemical Basis of Radiation Biology*, Taylor and Francis, London (1987)]. Since Nfo protein cleaves oxidized abasic sites efficiently, and regular abasic sites fairly well (Haring, 1994), it is likely that the abasic clusters we measure contain regular as well as oxidized abasic sites. Since Fpg protein cleaves oxidized abasic sites poorly (Haring, 1994), the clusters revealed by Fpg cleavage probably contain largely oxidized purine sites, with a minority of radiation-induced abasic sites. The Nth protein cleaves regular abasic sites well, but oxidized abasic sites poorly (Haring, 1994); thus the Nth-site clusters probably contain principally oxidized pyrimidine sites and ionizing radiation-induced regular abasic sites. Comparison of the cluster yields in FIG. 4 at a constant dose (e.g., 1 Gy) shows that the frequencies of the different cluster classes produced by γ-irradiation of DNA in phosphate buffer vary: normalized to the frequency of double strand breaks as 1, the ratios are 2 oxidized purine clusters: 1.5 abasic clusters: 0.56 oxidized pyrimidine clusters.

Since the Nth and Fpg proteins have multiple substrates (see FIG. 1), clusters revealed by treatment with these enzymes will include all substrate lesions in clusters that are recognized and DNA nicked under our conditions. In addition to the simple configurations shown, clustered lesions (including DSBs) may include other nearby damages. In model systems, clusters containing very closely spaced opposing damages (displaced by 1 base) may not be cleaved, or (displaced by 3 bases) cleaved poorly by lesion-recognizing enzymes, and the identity of the constituent partners and opposing bases can determine susceptibility to cleavage (Chaudhry and Weinfeld, 1997 and 1995; Harrison et al., 1998). These findings indicated that bases which were displaced by more than 3 bases (examples given were 5 bases) were cleaved efficiently. Additionally, in non-denaturing electrophoresis, opposing lesions separated by more than approximately 10–20 base pairs would not be expected to produce a DSB and hence under our conditions would not be detected as a cluster. Thus, the cluster levels measured may underestimate the total frequencies of multiple lesion sites that produce biological effects ascribed to clustered lesions.

Applicant also investigated whether lower energy photons produce clustered lesions and found that 50 kVp X-rays induced all four cluster classes in isolated DNA (see FIG. 3) although apparently in somewhat different ratios of frequencies of the classes than are produced by γ-rays.

Figure 5:
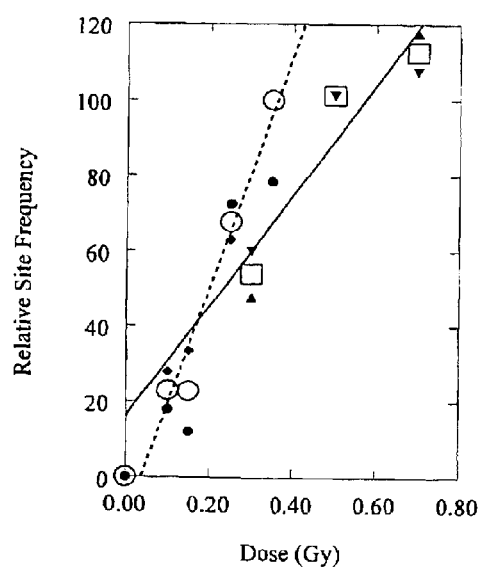
FIG. 5 is a graphical representation of the data on the induction of double strand breaks and oxidized pyrimidine clusters in human cells by low doses of 1 GeV/atomic mass unit $Fe^{+26}$ nuclei, normalized to the average frequency obtained for double strand breaks at 0.35 Gy (taken as 100%). Symbols: small, individual data (●and ♦, double strand breaks; ▲ and ▼, net Nth protein (oxidized pyrimidine) clusters; large, averages (○, double strand breaks; □, net oxidized pyrimidine clusters). Least squares lines are shown.

FIG. 4 shows that irradiation of DNA in solution induces clustered DNA damages. However, since the internal cellular milieu contains radical scavengers, ionizing radiation induces lower damage yields in intact cells than in isolated DNA [Oleinick et al., *Int. J. Radiation Biol.* 66: 523 (1994)]. However, the spatial condensation of DNA within cells compared to isolated DNA in solution might increase the production of clustered lesions. Studies were carried out to determine whether measurable levels of damage clusters were formed in cells irradiated with low doses of high LET radiation. FIG. 5 shows that irradiation of human cells with 0–0.70 Gy of 1 GeV/nucleon $Fe^{+26}$ ions produces somewhat comparable levels of DSBs and oxidized pyrimidine clusters. Thus, these data indicate that such clusters are formed at significant levels in human cells, even at low doses corresponding to cell survival >90%. Other results indicate that low LET radiation ($^{137}Cs$ γ-rays and 50 kVp X-rays) also produces at least one cluster class (oxidized purine clusters, recognized by Fpg cleavage) at yields comparable to DSB.

Clustered lesions are expected to constitute poorly repairable lesions that could produce mutations, induce inaccurate transcription, or constitute persistent lesions even in cells exposed to low levels of radiation. The mechanisms of repair of lesion clusters in cells are not yet clear, although studies with small oligonucleotides suggest possible pathways (Chaudhry and Weinfeld, 1997 and 1995; Harrison, 1998). In the cell, clusters may be subject to the same rejoining signals and pathways as are frank DSB. However, if one member of a cluster were repaired independently of opposing lesions, the same mechanisms that deal with isolated damages might prevail [Frosina, et al. *J. Biol. Chem.* 271: 9573 (1996); Demple, et al. *Proc. Natl. Acad. Sci. USA* 83: 7731 (1986)]. Further, the identity of the individual lesion in the cluster may dictate the repair path and susceptibility to repair by that path, and thus the severity of biological consequences of the cluster.

The assay method of the present invention has been used to show that clustered damages involving abasic sites and oxidized bases are induced in isolated DNA by ionizing radiation, both photons and particle radiation, and that such clusters comprise at least 80% of the total complex damages, with double strand breaks being only about 20%. The results using the assay method show that high LET radiation produces oxidized pyrimidine clusters in human cells. The present invention provides a foundation for correlating clustered DNA damages induced in cells, tissues or organisms by ionizing radiation or other DNA damaging agents with biological effects including survival, mutation and oncogenesis.

METHODS OF THE INVENTION

Irradiation and Enzyme Treatment of DNA in Solution

Bacteriophage T7 DNA in 20 mM K-phosphate buffer, pH 7.4, was irradiated in plastic tubes with $^{137}Cs$ γ-rays or 50 kVp X-rays. Samples were equilibrated with 70 mM HEPES/KOH, pH 7.6, 100 mM KCl, 1 mM EDTA, 1 mM DTT, 50 ng/µl bovine serum albumin. They were then treated with saturating levels (for reactions containing 500 ng T7 DNA, from 0–100 Gy, Fpg protein, 60 ng; Nth protein, 120 ng; Nfo protein, 156 ng) of a lesion-specific enzyme (FIG. 1) or without endonuclease for determination of frank double strand breaks (DSBs). After digestion with the lesion-specific enzyme was complete, traces of these enzymes were removed by addition of Proteinase K and EDTA to final concentrations of 1.33 mg/ml and 0.1 M, respectively, and incubation at 37° C. overnight. A neutral stop mixture (0.125% bromophenol blue, 0.5% sodium lauryl sulfate in 50% glycerol) was then added to insure dissociation of any persistent DNA-protein complexes.

Damage Cluster Measurement

Samples were electrophoresed along with molecular length standards (DNA from bacteriophages T4, λ and a HindIII digest of λ) in 0.4% agarose, in Tris-acetate buffer, pH 8, using static field electrophoresis (30 V, 6° C., with buffer recirculation) for cluster frequencies greater than approximately 30 sites/Mbp or unidirectional pulsed field electrophoresis (15V/cm; 0.3-s pulse, 10 s-interpulse, 16 hr, 10° C. with buffer recirculation) for lower cluster frequencies. Gels were stained with ethidium bromide (1 µg/ml), destained, and a quantitative electronic image obtained using a charge coupled device-based system (Sutherland et al., 1987). A DNA dispersion curve (migration position on the gel vs. molecular length) was constructed from the length standard DNA lanes. DNA lane profiles (fluorescence from ethidium bromide bound to DNA vs. migration distance) of the experimental samples were determined and their number average lengths were calculated. From these number average lengths, the frequencies of DSBs, $\phi_{DSB}$ (determined for DNA not treated with enzyme), and of other cluster sites, $\phi_c$ (determined by treatment with Nfo protein, Fpg protein, or Nth protein), were calculated from the equations (Freeman, 1986):

$$\phi_{DSB}=1/L_n(+\text{rad})-1/L_n(-\text{rad}) \text{ and} \qquad \text{Eq. 1}$$

$$\phi_c=1/L_n(+\text{rad}, +\text{enzyme})-1/L_n(+\text{rad}, -\text{enzyme}) \qquad \text{Eq. 2}$$

where $1/L_n(+\text{rad})$, $1/L_n(-\text{rad})$, $1/L_n(+\text{rad}, +\text{enzyme})$, and $1/L_n(+\text{rad},-\text{enzyme})$ are the reciprocals of the number average lengths of samples that were irradiated, unirradiated, irradiated and treated with enzyme, or irradiated and not treated with enzyme, respectively.

Clustered Damage Measurement in DNA from Irradiated Human Cells

Human monocytes (ATCC CRL 9855) were grown on Iscoves' modified Dulbecco's medium (Gibco/BRL, Grand Island N.Y.), 10% fetal bovine serum (Hyclone, Logan Utah) without antibiotics, and were ascertained to be free of mycoplasma by periodic testing (Bionique, Saranac Lake N.Y.). Cells in medium ($1\times10^6$ cells/0.25 ml in small vials, chilled on ice), were exposed to low doses (0–0.70 Gy) of 1 GeV/amu $\text{Fe}^{+26}$ ions (LET, 149 keV/amu) from the Brookhaven Alternating Gradient Synchrotron [Zeitlin et al., Radiation Res. 149: 560 (1998)]. Radiation doses were monitored by ionization chambers and beam uniformity by a scintillator/charge-coupled device camera system. Immediately after irradiation, cells were harvested by immersion of the vial into liquid nitrogen ($\text{LN}_2$) and stored in $\text{LN}_2$ until processed Each vial of frozen cells was thawed rapidly, EDTA was added to 83 mM final concentration, and the cell suspension was mixed with an equal volume of 2% agarose (InCert, FMC, Rockland Me.), and formed into plugs. The solidified plugs were treated with Lysis solution [10 mM Tris-Cl, 20 mM NaCl, 0.1 M EDTA, pH 8.3 (Lysis buffer) containing 1 mg/ml proteinase K (Boehringer Mannheim, Indianapolis Ind.), 0.2% n-lauroylsarcosine] for at least 96 hr with daily changes of Lysis solution. Digested plugs were rinsed with TE (10 mM Tris-HCl, 1 mM EDTA, pH 8) to remove detergent, treated with 10 volumes of TE containing 40 µg/ml phenylmethylsulfonyl fluoride (PMSF), and then rinsed 2× (30 min each) with TE, stored in L buffer (10 mM Tris-HCl, pH 8.0, 20 mM NaCl, 0.1 M EDTA), then digested with Not I (Lobrich, et al. Radiation Res. 138: 186 (1994)) (New England Biolabs, Beverly Mass.) according to the manufacturer's instructions. The effectiveness of NotI cleavage of DNA isolated by this method was determined by Southern blotting using a 1.7 kb ClaI-EcoRI probe to the third exon of the c-myc gene. Human DNA, along with molecular length standards, was dispersed on a 1% PFGE (Amresco, Solon Ohio) or FastLane (FMC) agarose transverse alternating field electrophoretic gel (Gardiner, et al. Somatic Cell Mol. Genet. 12: 185 (1986)) (TAFE; 30 min at 90 V with a 4 sec switching time, then 16 hr at 190 V with a 60 s switching time; electrophoresis buffer, 10 mM Tris acetate, 0.5 mM EDTA). The human DNA showed a single hybridizing band of 70 kb, the expected length of this fragment.

For glycosylase treatment, duplicate plugs from each experimental treatment were transferred to 70 mM HEPES-KOH, 100 mM KCl, 1 mM EDTA, pH 7.6, then to the same buffer containing 1 mM DTT, 10 mg/ml BSA. Plugs were then treated with sufficient lesion-specific enzyme (for 1 plug containing 500 ng DNA, 1.2 µg Nth protein) to cleave at all substrate sites. To remove traces of these enzymes, plugs were treated with Proteinase K (1 mg/ml) rinsed and equilibrated into electrophoresis buffer (10 mM Tris, 87 mM acetic acid, 0.5 mM EDTA free acid, pH 8). Samples were electrophoresed along with molecular length standard DNAs (Saccharomyces cerevisiae chromosomes, λ ladders) using neutral TAFE (Gardiner, et al. 1986). Gels were stained with ethidium bromide, destained, and an electronic image obtained. A DNA dispersion curve was determined using a spline fitting procedure, the number average lengths of the experimental DNAs calculated, and cluster lesion frequencies ($\phi_c$) in the 1.3 Mbp DNA populations computed according to Eq. 2 (Sutherland et al., 1996).

What is claimed is:

1. A method for detecting and quantifying clustered damages in DNA, the method comprising:
   a) providing a sample containing DNA to be assayed for clustered damages;
   b) contacting a first aliquot of the DNA to be tested for clustered damages with one or more lesion-specific cleaving reagents under conditions appropriate for cleavage of the DNA to produce single-strand nicks in the DNA at sites of damage lesions;
   c) quantitatively determining the number average molecular length ($L_n$) of double stranded DNA in the lesion-specific cleaving reagent-treated first aliquot;
   d) quantitatively determining the number average molecular length ($L_n$) of double stranded DNA in a second aliquot of the DNA to be tested for clustered damages, the second aliquot being untreated by lesion-specific cleaving reagents;
   e) calculating the frequency of clustered damages ($\Phi_c$) in the DNA to be assayed for clustered damages using the following equation:

$$\Phi_c=1/L_n(+\text{enzyme})-1/L_n(-\text{enzyme})$$

wherein $L_n(+\text{enzyme})$ is the number average molecular length of double stranded DNA determined for the lesion-specific leaving reagent-treated DNA determined in step c), and $L_n(-\text{untreated DNA in step d})$.

2. The method of claim 1 wherein the DNA sample is obtained from a biological organism.

3. The method of claim 1 wherein the DNA is genomic DNA.

4. The method of claim 1 wherein the number average molecular length of double stranded DNA is determined by:
   i) size fractionation of the DNA in an aliquot using non-denaturing gel electrophoresis; and
   ii) quantitative electronic imaging of the fractionated DNA produced in step i).

5. The method of claim 1 wherein the lesion-specific cleaving reagent is a chemical reagent capable of cleaving the phosphodiester bond of the DNA molecule at abasic sites.

6. The method of claim 1 wherein the lesion-specific cleaving reagent comprises lesion-specific enzyme.

7. The method of claim 6 wherein the lesion-specific enzymes comprise:
   a) a DNA glycosylase capable of cleaving the N-glycosyl bond of damaged nucleotides in a DNA molecule; and
   b) a DNA endonuclease capable of cleaving the phosphodiester bonds of the DNA molecule at abasic sites produced by the DNA glycosylase.

8. The method claim 6 wherein the lesion-specific enzymes comprise one or more enzymes capable of cleaning the phosphodiester bond of a DNA molecule at abasic sites.

9. The method of claim 7 or 8 wherein the lesion-specific enzyme capable of cleaving the phosphodiester bond of a DNA molecule at abasic sites is *E. coli* Nfo protein.

10. The method of claim 6 wherein the lesion-specific enzymes comprise enzymes capable of cleaving the N-glycosyl bond of damaged nucleotides in a DNA molecule and cleaving the phosphodiester bonds at the site of the damaged nucleotide.

11. The method of claim 10 wherein the lesion-specific enzymes comprise an enzyme which recognizes and cleaves DNA at sites of oxidized purines.

12. The method of claim 11 wherein the enzyme is *E. coli* formamidopyrimidine-DNA glycosylase.

13. The method of claim 10 wherein the lesion-specific enzymes comprise an enzyme which recognizes and cleaves DNA at sites of oxidized pyrimidines.

14. The method of claim 13 wherein the enzyme is *E. coli* Nth protein.

15. The method of claim 6 wherein the lesion-specific enzymes comprises:
   a) Fpg protein; and
   b) endonuclease III.

16. The method of claim 6 wherein the lesion-specific enzymes comprises:
   a) Fpg protein; and
   b) endonuclease IV.

17. The method of claim 6 wherein the lesion-specific enzymes comprises:
   a) endonuclease III; and
   b) endonuclease IV.

18. The method of claim 6 wherein the lesion-specific enzymes comprises:
   a) endonuclease III;
   b) endonuclease IV; and
   c) Fpg protein.

19. A method for detecting and quantifying clustered damages in DNA of a biological organism induced by exposure of the biological organism to a DNA-damaging agent, the method comprising:

a) providing a first sample of DNA obtained from the biological organism prior to exposure to a DNA-damaging agent, and a second sample of DNA obtained from the biological organism after exposure to a DNA damaging agent;
   b) assaying each sample for clustered damages in the DNA by performing steps b) through e) of claim 1 on each sample; and
   c) subtracting the frequency of clustered damages ($\Phi_c$) determined for the first sample, from the frequency of clustered damages determine for the second sample, to produce a value representative of the clustered DNA damage induced by exposure of the biological organism to the DNA-damaging agent.

20. The method of claim 19 wherein the number average molecular length of double stranded DNA is determined by:
   i) size fractionation of the DNA in an aliquot using non-denaturing gel electrophoresis; and
   ii) quantitative electronic imaging of the fractionated DNA produced in step i).

21. The method of claim 19 wherein the DNA-damaging agent is X-rays.

22. The method of claim 19 wherein the DNA-damaging agent is Y-rays.

23. The method of claim 19 wherein the DNA-damaging agent is radon.

24. The method of claim 19 wherein the DNA-damaging agent is a known carcinogen.

25. A method for detecting an accumulation of clustered damages in DNA of a biological organism, the method comprising determining the frequency of clustered damages in each DNA sample in a plurality of DNA samples obtained from a biological organism over a specified period of time by the method of claim 1, and comparing the determined frequencies to one another to detect an accumulation of clustered damages in the biological organism over the period of time.

26. The method of claim 25 wherein the biological organism is exposed to one or more DNA damaging agents over the period of time.

27. The method of claim 26 wherein the DNA damaging agent is ionizing radiation.

* * * * *

UNITED STATES PATENT AND TRADEMARK OFFICE
CERTIFICATE OF CORRECTION

PATENT NO. : 6,789,022 B2
APPLICATION NO. : 09/837560
DATED : September 7, 2004
INVENTOR(S) : Betsy M. Sutherland It is certified that error appears in the above-identified patent and that said Letters Patent is hereby corrected as shown below:

1. Column 14: in Claim 1, line 43, delete "leaving" and insert -- cleaving --.

2. Column 15: in Claim 8, line 2, delete "cleaning" and insert -- cleaving --.

3. Column 16: in Claim 19, line 11, delete "determine" and insert -- determined --.

4. Column 16: in Claim 22, line 24, delete "Y-rays" and insert -- $\gamma$-rays --.

Signed and Sealed this

Fourteenth Day of August, 2007

JON W. DUDAS
*Director of the United States Patent and Trademark Office*